United States Patent
Gelvin

(10) Patent No.: US 9,655,777 B2
(45) Date of Patent: May 23, 2017

(54) SYSTEM AND METHOD FOR DIAGPHRAGM PUMPING USING HEATING ELEMENT

(71) Applicant: Novartis AG, Basel (CH)

(72) Inventor: Michael LeRoy Gelvin, Alta Loma, CA (US)

(73) Assignee: Novartis AG, Basel (CH)

( * ) Notice: Subject to any disclaimer, the term of this patent is extended or adjusted under 35 U.S.C. 154(b) by 309 days.

(21) Appl. No.: 14/680,375

(22) Filed: Apr. 7, 2015

(65) Prior Publication Data

US 2016/0296371 A1    Oct. 13, 2016

(51) Int. Cl.
*A61M 5/00* (2006.01)
*A61F 9/007* (2006.01)

(52) U.S. Cl.
CPC .............................. *A61F 9/00781* (2013.01)

(58) Field of Classification Search
CPC .................................................. A61F 9/00781
See application file for complete search history.

(56) References Cited

U.S. PATENT DOCUMENTS

| 4,089,329 | A | 5/1978 | Couvillon, Jr. et al. |
| 4,206,762 | A | 6/1980 | Cosman |
| 4,457,757 | A | 7/1984 | Molteno |
| 4,656,827 | A | 4/1987 | Puillet |
| 4,750,901 | A | 6/1988 | Molteno |
| 4,869,282 | A | 9/1989 | Sittler et al. |
| 4,922,913 | A | 5/1990 | Waters, Jr. et al. |
| 5,005,577 | A | 4/1991 | Frenkel |
| 5,083,742 | A | 1/1992 | Wylie et al. |
| 5,178,604 | A | 1/1993 | Baerveldt et al. |
| 5,179,953 | A | 1/1993 | Kursar |
| 5,397,300 | A | 3/1995 | Baerveldt et al. |
| 5,466,233 | A | 11/1995 | Weiner et al. |
| 5,476,445 | A | 12/1995 | Baerveldt et al. |
| 5,558,629 | A | 9/1996 | Baerveldt et al. |

(Continued)

FOREIGN PATENT DOCUMENTS

| DE | 4438201 | 5/1996 |
| EP | 0102747 | 3/1984 |

(Continued)

OTHER PUBLICATIONS

Byunghoon Bae, Hongseok Kee, Seonho Kim, Yeon Lee, Taeseok Sim, Yongkweon Him and Kyihwan Park; "In Vitro Experiment of the Pressure Regulating Valve for a Glaucoma Impact"; Journal of Micromechanics and Microengineering, 13 (2003); pp. 613-619.

(Continued)

*Primary Examiner* — Leslie Deak
(74) *Attorney, Agent, or Firm* — Kenneth D. Bassinger

(57) ABSTRACT

Systems and methods for treating an ocular condition includes a heating chamber comprising a material expandable when heated and comprising a flow passage having an inlet and an outlet. A heating element is arranged and disposed to introduce heat in the heating chamber. A flexible diaphragm separates the heating chamber from the flow passage, and is moveable between a first position and a second position to change a volume of one of the pump chamber and flow passages in response to a temperature change in the heating chamber.

20 Claims, 5 Drawing Sheets

(56) References Cited

U.S. PATENT DOCUMENTS

| | | |
|---|---|---|
| 5,707,643 A | 1/1998 | Ogura et al. |
| 5,910,110 A | 6/1999 | Bastable |
| 6,007,511 A | 12/1999 | Prywes |
| 6,048,328 A | 4/2000 | Haller et al. |
| 6,251,090 B1 | 6/2001 | Avery et al. |
| 6,447,449 B1 | 9/2002 | Fleischman et al. |
| 6,468,283 B1 | 10/2002 | Richter et al. |
| 6,579,235 B1 | 6/2003 | Abita et al. |
| 6,589,198 B1 | 7/2003 | Soltanpour et al. |
| 6,682,500 B2 | 1/2004 | Soltanpour et al. |
| 6,712,764 B2 | 3/2004 | Jeffries et al. |
| 6,719,750 B2 | 4/2004 | Varner et al. |
| 6,749,568 B2 | 6/2004 | Fleischman et al. |
| 6,939,299 B1 | 9/2005 | Petersen et al. |
| 6,976,982 B2 | 12/2005 | Santini, Jr. et al. |
| 7,137,952 B2 | 11/2006 | Leonardi et al. |
| 7,169,106 B2 | 1/2007 | Fleischman et al. |
| 7,252,006 B2 | 8/2007 | Tai et al. |
| 7,354,416 B2 | 4/2008 | Quiroz-Mercado et al. |
| 7,409,863 B2 | 8/2008 | Bateman et al. |
| 7,612,328 B2 | 11/2009 | Kaiser |
| 7,756,559 B2 | 7/2010 | Abreu |
| 8,182,435 B2 | 5/2012 | Dacquay et al. |
| 8,257,295 B2 | 9/2012 | Rickard et al. |
| 8,419,673 B2 | 4/2013 | Rickard |
| 8,821,430 B2 * | 9/2014 | Stergiopulos .......... A61B 17/12 604/9 |
| 2001/0000527 A1 | 4/2001 | Yaron et al. |
| 2002/0019607 A1 | 2/2002 | Bui |
| 2002/0049374 A1 | 4/2002 | Abreu |
| 2002/0099359 A1 | 7/2002 | Santini, Jr. et al. |
| 2002/0139947 A1 | 10/2002 | Wang |
| 2002/0143284 A1 | 10/2002 | Tu et al. |
| 2002/0193674 A1 | 12/2002 | Fleischman et al. |
| 2003/0014036 A1 | 1/2003 | Varner et al. |
| 2003/0078487 A1 | 4/2003 | Jeffries et al. |
| 2003/0225318 A1 | 12/2003 | Montegrande et al. |
| 2004/0059248 A1 | 3/2004 | Messner et al. |
| 2004/0073137 A1 | 4/2004 | Lloyd et al. |
| 2004/0111050 A1 | 6/2004 | Smedley et al. |
| 2004/0116794 A1 | 6/2004 | Fink et al. |
| 2004/0186367 A1 | 9/2004 | Fresco |
| 2004/0254438 A1 | 12/2004 | Chuck et al. |
| 2004/0254517 A1 | 12/2004 | Quiroz-Mercado et al. |
| 2005/0049578 A1 | 3/2005 | Tu et al. |
| 2005/0159660 A1 | 7/2005 | Montegrande et al. |
| 2005/0271704 A1 | 12/2005 | Tu et al. |
| 2005/0273033 A1 | 12/2005 | Grahn et al. |
| 2006/0131350 A1 | 6/2006 | Schechter et al. |
| 2007/0019156 A1 | 1/2007 | Fink |
| 2007/0032757 A1 | 2/2007 | Medow et al. |
| 2007/0077270 A1 | 4/2007 | Wen |
| 2007/0106199 A1 | 5/2007 | Krivoy et al. |
| 2007/0106200 A1 | 5/2007 | Levy |
| 2007/0109117 A1 | 5/2007 | Heitzmann et al. |
| 2007/0123767 A1 | 5/2007 | Montegrande et al. |
| 2007/0129623 A1 | 6/2007 | Fleischman et al. |
| 2007/0212397 A1 | 9/2007 | Roth |
| 2008/0015421 A1 | 1/2008 | Penner |
| 2008/0027478 A1 | 1/2008 | Connors et al. |
| 2008/0077127 A1 | 3/2008 | Gao et al. |
| 2008/0097276 A1 | 4/2008 | Bertrand et al. |
| 2008/0125691 A1 | 5/2008 | Yaron et al. |
| 2008/0129486 A1 | 6/2008 | Jeckelmann et al. |
| 2008/0147021 A1 | 6/2008 | Jani |
| 2008/0228127 A1 | 9/2008 | Burns et al. |
| 2009/0069648 A1 | 3/2009 | Irazoqui et al. |
| 2009/0076367 A1 | 3/2009 | Sit et al. |
| 2009/0143713 A1 | 6/2009 | Van Dam et al. |
| 2009/0227933 A1 | 9/2009 | Karageozian |
| 2009/0240215 A1 | 9/2009 | Humayun et al. |
| 2009/0275924 A1 | 11/2009 | Lattanzio et al. |
| 2009/0312742 A1 | 12/2009 | Pang et al. |
| 2010/0010416 A1 | 1/2010 | Juan, Jr. et al. |
| 2010/0042209 A1 | 2/2010 | Guarnieri |
| 2010/0121248 A1 | 5/2010 | Yu et al. |
| 2010/0121348 A1 | 5/2010 | van der Burg et al. |
| 2010/0174272 A1 | 7/2010 | Weiner |
| 2010/0222769 A1 | 9/2010 | Meng et al. |
| 2010/0234717 A1 | 9/2010 | Wismer |
| 2010/0253167 A1 | 10/2010 | Charnley et al. |
| 2010/0305550 A1 | 12/2010 | Meng et al. |
| 2011/0046536 A1 | 2/2011 | Stegmann et al. |
| 2011/0071454 A1 | 3/2011 | Dos Santos et al. |
| 2011/0071456 A1 | 3/2011 | Rickard |
| 2011/0071505 A1 | 3/2011 | Rickard et al. |
| 2011/0248671 A1 | 10/2011 | Dos Santos et al. |
| 2012/0089072 A1* | 4/2012 | Cunningham, Jr. A61F 9/00781 604/9 |

FOREIGN PATENT DOCUMENTS

| | | |
|---|---|---|
| EP | 2427097 | 3/2012 |
| WO | 9303665 | 3/1993 |
| WO | 9803665 | 1/1998 |
| WO | 9803809 | 1/1998 |
| WO | 9938470 | 8/1999 |
| WO | 0194784 | 12/2001 |
| WO | 02056758 | 7/2002 |
| WO | 03001991 | 1/2003 |
| WO | 03102632 | 12/2003 |
| WO | 2004014218 | 2/2004 |
| WO | 2005079204 | 9/2005 |
| WO | 2005088417 | 9/2005 |
| WO | 2007127305 | 11/2007 |
| WO | 2007136993 | 11/2007 |
| WO | 2008061043 | 5/2008 |
| WO | 2008084350 A2 | 7/2008 |
| WO | 2009010799 | 1/2009 |
| WO | 2009026499 | 2/2009 |
| WO | 2009049686 | 4/2009 |
| WO | 2009081031 | 7/2009 |
| WO | 2010129446 | 11/2010 |
| WO | 2011034727 | 3/2011 |
| WO | 2011034738 | 3/2011 |
| WO | 2011034740 | 3/2011 |
| WO | 2011034742 A2 | 3/2011 |
| WO | 2011035218 | 3/2011 |
| WO | 2011034742 A3 | 5/2011 |
| WO | 2012012017 | 1/2012 |

OTHER PUBLICATIONS

Driot et al.; "Ocular pharmacokinetics of fluocinolone acetonide after RetisertTM intravitreal implantation in rabbits over a 1-year period"; J. Ocular Pharm; vol. 20; No. 3; pp. 269-275 (2004).

Eggers, T., et al, "Wireless Intra-Ocular Pressure Monitoring System Integrated Into an Artificial Lens," 1st Annual Int'l IEEE-EMBS Special Topic Conference on Microtechnologies in Medicine & Biology, Oct. 12-14, 2000, pp. 466-469, Lyon, France.

Glybina et al.; "Neuroprotective properties of fluocinolone acetonide chronically delivered into the vitreous of albino RCS rats"; IVOS; vol. 47; ARVO E-Abstract 1028 (2006).

Greene, M.E. and Gilman, B.G., "Intraocular Pressure Measurement With Instrumented Contact Lenses," Investigative Ophthalmology & Visual Science (IVOS), Apr. 1974, pp. 299-302, vol. 13, No. 4, IVOS.

Hjortdal, Jesper and Jensen, Peter, "In Vitro Measurement of Corneal Strain, Thickness, and Curvature Using Digital Image Processing," Acta Ophthalmologica Scandinavica, 1995, pp. 5-11, vol. 73, Denmark.

International Searching Authority, Search Report and Written Opinion of the International Searching Authority, PCT/US2012/067741, Jul. 9, 2013, 12 pages.

International Searching Authority, Search Report and Written Opinion of the International Searching Authority PCT US2010/047605, Dec. 16, 2010.

International Searching Authority, Search Report and Written Opinion of the International Searching Authority PCT/US2010/047612, Dec. 21, 2010.

(56) References Cited

OTHER PUBLICATIONS

International Searching Authority, Search Report and Written Opinion of the International Searching.Authority PCT/US2012/067747, dated Apr. 2, 2013.
International Searching Authority, Search Report and Written Opinion of the International Searching Authority PCT/US2012/068878, dated Apr. 3, 2013.
International Searching Authority, Search Report and Written Opinion of the International Searching Authority, PCT/US2010/033329, Jul. 13, 2010, 14 pages.
International Searching Authority, Search Report and Written Opinion of the International Searching Authority, PCT/US2010/047429, Nov. 1, 2010, 15 pages.
International Searching Authority, Search Report and Written Opinion of the International Searching Authority, PCT/US2010/047600, Dec. 14, 2010, 13 pages.
International Searching Authority, Search Report and Written Opinion of the International Searching.Authority, PCT/US2010/049424, Nov. 26, 2010, 15 pages.
International Searching Authority, Search Report and Written Opinion of the International Searching Authority, PCT/US2011/036742, Aug. 17, 2011, 2 pages.
Kuppermann, B D et al., 2006, "Efficacy and safety of a novel intravitreous dexamethasone drug-delivery system after applicator or incisional placement in patients with macular edema", IVOS, vol. 47 ARVO E-Abstract 5913 (2006).
Lam, Andrew K.C. and Douthwaite, William A., "The Effect of an Artificially Intraocular Pressure on the Central Corneal Curvature," Ophthalmic and Physiological Optics, 1997, pp. 18-24, vol. 17, No. 1, Elsevier Science, Ltd., Great Britain.
Leonardi, Matteo, et al., "A Soft Contact Lens With a Mems Strain Gage Embedded for Intraocular Pressure Monitoring," In Proc. 12th Int'l Conference on Solid State Sensors, Actuators and Microsystems, Jun. 8-12, 2003, pp. 1043-1046, vol. 2, Boston, MA.
Leonardi, Matteo, et al., "First Steps Toward Noninvasive Intraocular Pressure Monitoring with a Sensing Contact Lens," Investigative Ophthalmology & Visual Science (IVOS), 2004, pp. 3113-3117, vol. 45, No. 9, IVOS.
McLaren, Jay W., et al, "Continuous Measurement of Intraocular Pressure in Rabbits by Telemetry," Investigative Ophthalmology & Visual Science (IVOS), May 1996, pp. 966-975, vol. 37, No. 6, IVOS.
Miyamoto, H et al., Biodegradable scleral implant for intravitreal controlled release of fluconazole, Current Eye Res., 1997, vol. 16, No. 19, pp. 930-935.
Mokwa, Wilfried, et al, "Micro-Transponder Systems for Medical Applications," IEEE Transactions on Instrumentation and Measurement, Dec. 2001, pp. 1551-1555, vol. 50, No. 6, IEEE, Germany.
Mruthyunjaya, P et al., "An intravitreal sustained release fluocinolone acetonide device to treat severe experimental uveitis", IOVS, 2003, vol. 44, ARVO E-Abstract 4215.
Neagu, Cristina R.; "A Medical Microactuator Based on an Electrochemical Principle"; Thesis at the Twente University, the Netherlands, Enschede; Aug. 28, 1998; pp. 1-162.
Nisar, et al.; MEMS-Based Micropumps in Drug Delivery and Biomedical Applications; ScienceDirect; Sensors and Actuators B 130; 2008, pp. 917-942.
Puers, Robert, "Linking Sensors with Telemetry: Impact on the System Design," In Proc. 8th Int'l Conference of Solid State Sensors, Actuators, Eurosens, Jun. 25-29, 1995, pp. 169-174, Stockholm, Sweden.
Ratanapakorn, T et al., "Helical intravitreal triamcinolone implant: An explanation survival study", IVOS, 2005, vol. 46 ARVO E-Abstract 484.
Rego, MGR et al., "In vitro evaluation of sustained-release intravitreal dexamethasone implants", IVOS, 2004, vol. 45, ARVO E-Abstract 5060.
Sakurai, E et al., "Scleral plug of biodegradable polymers containing ganciclovir for experimental cytomegalovirus retinitis", IVOS, 2001, vol. 42, No. 9, pp. 2043-2048.
Saloomeh, Saati M.D., et al.; "Mini Drug Pump for Ophthalmic Use"; Trans Am Ophthalmol Soc 2009; 107; pp. 60-71.
Schnakenberg, U., et al, "Initial Investigations on Systems for Measuring Intraocular Pressure," Sensors and Actuators, 2000, p. 287-291, vol. 85, Elsevier Science B.V., Germany.
See, R F et al., "Safety and drug release profile of injectable intravitreal sustained-release fluocinolone acetonide device", IVOS, 2006, vol. 47, ARVO E-Abstract 5119.
Stangel, Karsten, et al, "A Programmable Intraocular CMOS Pressure Sensor System Implant," IEEE Journal of Solid-State Circuits, Jul. 2001, pp. 1094-1100, vol. 36, No. 7, IEEE, Germany.
Stemme, et al.; "A Valveless Diffuser/Nozzle-Based Fluid Pump"; ScienceDirect; Sensors and Actuators A, 1993, 39, pp. 159-167.
Tano, R et al., Helical intravitreal implant: surgical method development and outcomes, IVOS, 2005,vol. 46, ARVO E-Abstract 483.
Ullerich, Stella, et al, "Micro Coils for an Advanced System for Measuring Intraocular Pressure," 1st Annual Int'l IEEE-EMBS Special Topic Conference on Microtechnologies in Medicine & Biology, Oct. 12-14, 2000, pp. 470-474, Lyon, France.
Van Schuylenbergh, K., et al, "An Implantable Telemetric Tonometer for Direct Intraocular Pressure Measurements," 1st European Conference on Biomedical Engineering, Feb. 1991, pp. 194-195, vol. 17, No. 20, Nice, France.
Varner, S E et al., "Development of a minimally invasive intravitreal implant for drug delivery", IVOS, 2003, vol. 44, ARVO E-Abstract 4214.
Walter, Peter; Intraocular Pressure Sensor: Where Are We—Where Will We Go? Journal Graefe's Archive for Clinical and EIDSperimental Ophthalmology; Publisher Springer Berline/ Heidelberg; ISSN 0721-832IDS (Print) 1435-702IDS (Online); Issue vol. 240, No. 5/May 2002 DOI 10.1007/s00417-002-0474-y; pp. 335-336; Subject Collection Medicine.
Weiner, A L, 2007, "Drug Delivery Systems in Ophthalmic Applications, In: Ocular Therapeutics; Eye on New Discoveries; T. Yorio, A. Clark, M.WaIDS, Eds, Elsevier Press/Academic Press, New York", 2007, pp. 7-43.
Yasukawa, T et al., "Biodegradable scleral plugs for vitreoretinal drug delivery", Adv. Drug Del Rev., 2001, vol. 52, No. 1, pp. 25-36.

* cited by examiner

SYSTEM AND METHOD FOR DIAGPHRAGM PUMPING USING HEATING ELEMENT

BACKGROUND

The present disclosure relates generally to pressure/flow control systems and methods for use in treating a medical condition. In some instances, embodiments of the present disclosure are configured to be part of an IOP control system for the treatment of ophthalmic conditions.

Glaucoma, a group of eye diseases affecting the retina and optic nerve, is one of the leading causes of blindness worldwide. The chamber pressure of the eye is known as intraocular pressure (IOP). Most forms of glaucoma result when IOP increases to pressures above normal for prolonged periods of time. IOP can increase due to high resistance to the drainage of the aqueous humor relative to its production. Left untreated, an elevated IOP causes irreversible damage to the optic nerve and retinal fibers resulting in a progressive, permanent loss of vision. This may be due to a direct effect of the raised pressure upon the optic nerves and/or the effect of chronic under-perfusion of the nerve head.

The eye's ciliary body continuously produces aqueous humor, the clear fluid that fills the anterior segment of the eye (the space between the cornea and lens). The aqueous humor flows out of the anterior chamber (the space between the cornea and iris) through the canalicular and the uveoscleral pathways, both of which contribute to the aqueous drainage system. The orbital globe of the eye is an essentially non-compliant sphere, allowing IOP to be influenced by a change in volume of the contents of the orbit, including both the anterior segment and the posterior segment. Thus, the delicate balance between the production and drainage of aqueous humor can influence the IOP of the eye.

FIG. 1 is a diagram of the front portion of an eye 10 that helps to explain the processes of glaucoma. In FIG. 1, representations of the lens 110, cornea 120, iris 130, ciliary body 140, trabecular meshwork 150, Schlemm's canal 160, the anterior segment 165 including both the anterior chamber 170 and the posterior chamber 175, the posterior segment 178, the sclera 180, the retina 182, the choroid 185, the limbus 190, the suspensory ligaments or zonules 195, the suprachoroidal space 200, and the conjunctiva 202 are pictured. Aqueous fluid is produced by the ciliary body 140, which lies beneath the iris 130 and adjacent to the lens 110 in the anterior chamber 170 of the anterior segment of the eye 165. This aqueous humor washes over the lens 110 and iris 130 and flows to the drainage system located in the angle of the anterior chamber 170. The posterior segment 178 is filled with a gel-like substance called vitreous humor. Normal regulation of IOP occurs chiefly through the regulation of the volume of aqueous humor. Similarly, however, changes in the volume of fluid (e.g., vitreous humor) within the posterior segment can affect IOP.

After production by the ciliary body 140, the aqueous humor may leave the eye by several different routes. Some goes posteriorly through the vitreous body behind the lens 110 to the retina, while most circulates in the anterior segment of the eye to nourish avascular structures such as the lens 110 and the cornea 120 before outflowing by two major routes: the conventional outflow pathway route 205 and the uveoscleral outflow route 210. The angle of the anterior chamber 170, which extends circumferentially around the eye, contains structures that allow the aqueous humor to drain. The conventional outflow pathway (or trabecular meshwork) route is the main mechanism of outflow, accounting for a large percentage of aqueous egress. The route extends from the anterior chamber angle (formed by the iris 130 and the cornea 120), through the trabecular meshwork 150, into Schlemm's canal 160. The trabecular meshwork 150, which extends circumferentially around the anterior chamber 170, is commonly implicated in glaucoma. The trabecular meshwork 150 seems to act as a filter, limiting the outflow of aqueous humor and providing a back pressure that directly relates to IOP. Schlemm's canal 160 is located just peripheral to the trabecular meshwork 150. Schlemm's canal 160 is fluidically coupled to collector channels (not shown) allowing aqueous humor to flow out of the anterior chamber 170. The arrows 205 show the flow of aqueous humor from the ciliary bodies 140, over the lens 110, over the iris 130, through the trabecular meshwork 150, and into Schlemm's canal 160 and its collector channels (to eventually reunite with the bloodstream in the episcleral vessels (not shown)).

The uveoscleral route 210 accounts for the major remainder of aqueous egress in a normal eye, and also begins in the anterior chamber angle. Though the anatomy of the uveoscleral route 210 is less clear, aqueous is likely absorbed by portions of the peripheral iris 130, and the ciliary body 140, after which it passes into the suprachoroidal space 200. The suprachoroidal space 200 is a potential space of loose connective tissue between the sclera 180 and the choroid 185 that provides a pathway for uveoscleral outflow. Aqueous exits the eye along the length of the suprachoroidal space to eventually reunite with the bloodstream in the episcleral vessels.

One method of treating glaucoma includes implanting a drainage device in a patient's eye. The drainage device allows fluid to flow from the interior of the eye (e.g., from the posterior segment to a drainage site, relieving pressure in the eye and thus lowering IOP). The system and methods disclosed herein overcome one or more of the deficiencies of the prior art.

SUMMARY

According to an exemplary aspect, the present disclosure is directed to a system for treating an ocular condition including a heating chamber comprising a material expandable when heated and comprising a flow passage having an inlet and an outlet. A heating element is arranged and disposed to introduce heat in the heating chamber. A flexible diaphragm separates the heating chamber from the flow passage, and is moveable between a first position and a second position to change a volume of one of the pump chamber and flow passages in response to a temperature change in the heating chamber.

In an aspect, the heating element is a resistive heating element configured to increase in temperature when a current is passed therethrough. In an aspect, the heating element is disposed within the pump chamber. In an aspect, the heating element is a resistive heating element disposed along a wall of the heating chamber opposite the flexible diaphragm. In an aspect, the system includes a power source and a feed wire extending on opposing sides of the heating element, the feed wire being in electrical communication with the power source. In an aspect, the system includes at least one sensor arranged to detect a pressure indicative of intraocular pressure. In an aspect, the system includes a processor configured to operate the heating element based on information detected by the at least one sensor. In an aspect, the system includes a first one-way valve and a second one-way valve operable as the flexible diaphragm moves from the first position to the second position and back to the first position to promote the passage of drainage fluid through the flow passage in one direction. In an aspect, the first and second check valves are reed valves or flapper valves.

According to another exemplary aspect, the present disclosure is directed to a system implantable in an eye for treating an ocular condition. The system includes a housing sized for implantation in an eye of a patient, comprising: a sealed heating chamber; and a fluid flow passage having an inlet and an outlet. The system also includes a flexible diaphragm carried by the housing and disposed between and separating the heating chamber from the fluid flow passage and includes a heating element arranged and disposed to induce heat in the heating chamber to change pressure in the chamber. A power source may be in electrical communication with the heating element and configured to induce electrical current in the heating element.

In another exemplary aspect, the present disclosure is directed to a method for treating an ocular condition comprising: inducing flow of a liquid through a flow pump having a flexible diaphragm separating a flow passage from a heating chamber; moving the flexible diaphragm from a first position to a second position by increasing a temperature of a fluid in the heating chamber; forcing fluid from the flow passage as the flexible diaphragm moves the first position to the second position; and drawing fluid into the flow passage by moving the flexible diaphragm from the second position to the first position.

In an aspect, moving the flexible diaphragm by increasing a temperature of a fluid in the heating chamber comprises applying voltage to a heating element disposed in a closed chamber. In an aspect, the method includes drawing fluid into the flow passage through a first one-way valve and pushing fluid out of the flow passage through a second one-way valve. In an aspect, the method includes implanting the flow pump in an eye of a patient.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

Figure 1:
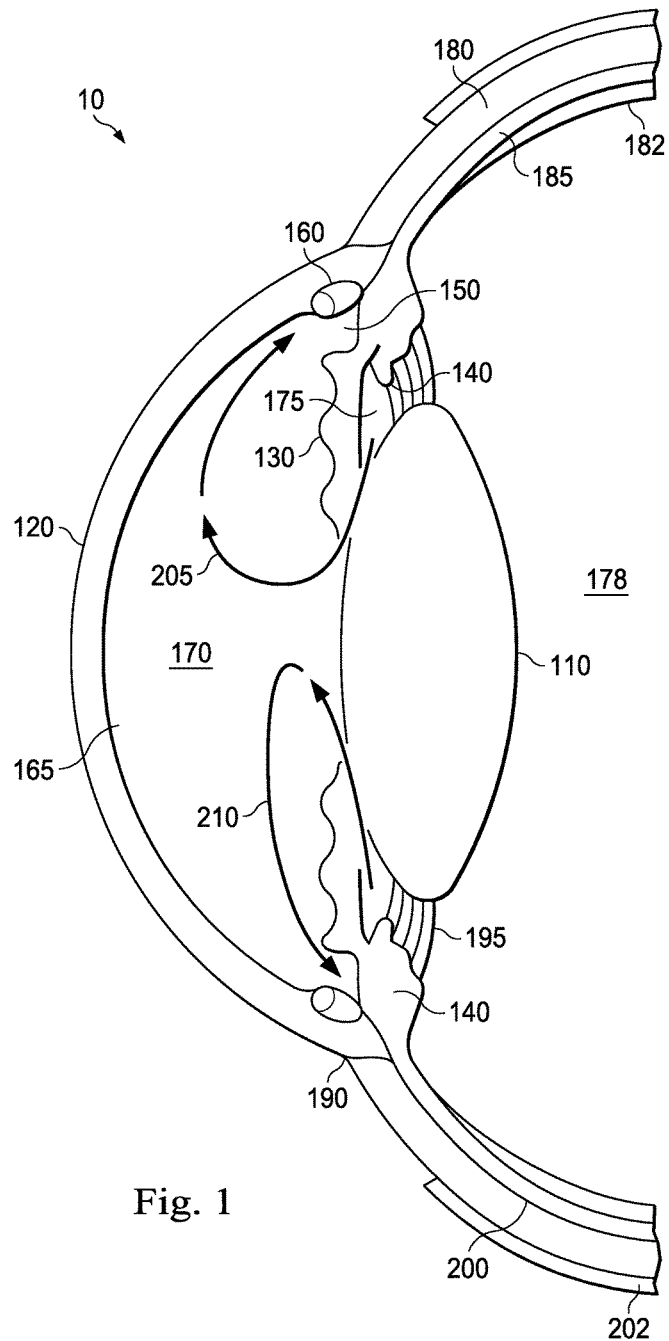
FIG. 1 is a diagram of the front portion of an eye.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

The present disclosure is directed to a flow control system for treating a medical condition, such as glaucoma, by using a heat generating resistive element within an intraocular implant to create a pumping action usable to transfer or pump fluid. In one aspect, the system may use this pumping action to adjust IOP by regulating fluid drainage through the intraocular implant, such as a glaucoma drainage device (GDD). Since the system employs a diaphragm that flexes in cycles and cooperates with check valves to generate pumping action, the system may be actuated and may recover more quickly than other types of pump systems, such as those using electrolysis to create air bubbles. Thus, the flow control systems and methods disclosed herein allow the flow control system to pump aqueous solutions to control IOP while maintaining responsiveness unachieved in traditional GDDs.

Figure 2:
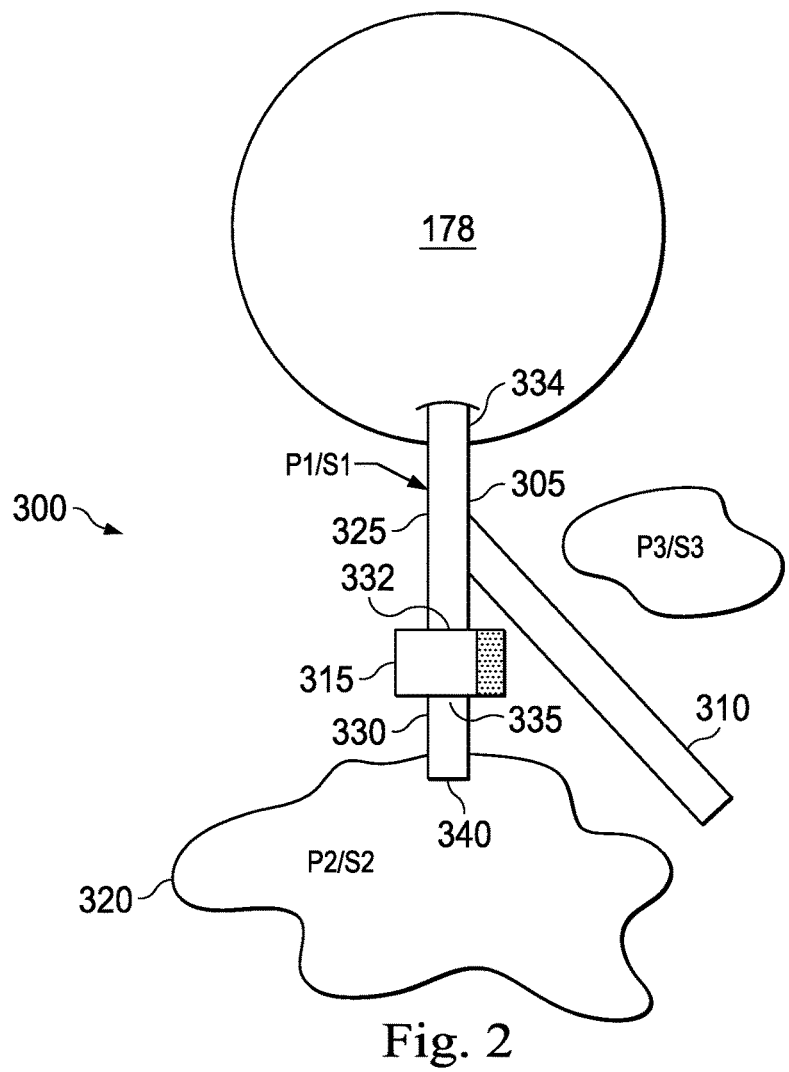
FIG. 2 is a schematic diagram of an exemplary drainage device disposed on an eye according to the principles of the present disclosure.

FIG. 2 is a schematic diagram of an exemplary drainage device or implant 300 positioned within an eye of a patient. The drainage implant 300 is designed to regulate IOP by utilizing an adjustable smart valve or active element (e.g., without limitation, a pump) to throttle or pump fluid out of a posterior segment 178 into a drainage site.

In the embodiment pictured in FIG. 2, the implant 300 is arranged in the eye such that three areas of pressure interact with the implant: P1, P2, and P3. Pressure area P1 reflects the pressure of the posterior segment 178, pressure area P2 reflects the pressure of a drainage site 320, and pressure area P3 reflects a pressure located remotely from P1 and P2 (effectively reflecting atmospheric pressure). In some embodiments, pressure area P1 reflects the pressure located in a lumen or tube that is in fluidic communication with the posterior segment 178.

In FIG. 2, the implant 300 includes a drainage tube 305 and a divider 310 associated with a flow controller 315. The drainage tube 305 drains fluid from the posterior segment 178 of the eye to the drainage location 320, which may be the suprachoroidal space 200 shown in FIG. 1. Other examples of a drainage location 320 include, but are not limited to: a subconjunctival space, a subscleral space, a supraciliary space, an episcleral vein, and other uveoscleral pathways. The drainage tube 305 includes an inlet tube or inlet tube portion 325, which extends from the posterior segment 178 to the flow controller 315, and an outlet tube or outlet tube portion 330, which extends from the flow controller 315 to the drainage site 320. The inlet tube 325 includes a proximal end 332 coupled to the flow controller 315 and a distal end 334 positioned within the posterior segment 178. The outlet tube 330 includes a proximal end 335 coupled to the flow controller 315 and a distal end 340 positioned within the drainage site 320.

The flow controller 315 regulates IOP by controlling, such as by throttling or inducing the flow of fluid, through the tube 305, from the inlet tube 325 to the outlet tube 330. In some instances, the flow controller 315 throttles the flow of fluid through the tube 305 as a function of a pressure differential. The flow controller 315 may include components or elements, such as valves, pumps or others, described further below with reference to FIG. 3, that control pressure by regulating the amount of drainage flow through the implant 300. The flow controller 315 may include any number of valves and any number of pumps, or may not include a pump or may not include a valve. In some embodiments, the flow controller 315 is an active system that is responsive to signals from a processor to increase flow, decrease flow, or to maintain a steady flow as a function of pressure differentials at pressure areas P1, P2, and P3. In one embodiment, it does this by actuating a pump to increase or decrease the fluid flow passage through the flow controller 315.

In addition, the flow controller 315 may incorporate pressure sensors to monitor and utilize the pressures P1, P2, and P3 to achieve a desired IOP. In some embodiments, the implant 300 responds to the pressure differentials between the pressures sensed at P1, P2, and P3 by sensors S1, S2, and S3, respectively, to control the flow controller 315 and thereby throttle the flow rate of fluid through the drainage tube 305 to control IOP. In some embodiments, the various pressure differentials across the pressure areas sensed at P1, P2, and P3 (P1-P2, P1-P3, P2-P3) drive the flow controller 315 and dictate the valve position or pump state to throttle the flow rate of fluid through the drainage tube 305 to control IOP. In some embodiments, the implant may include only a pressure sensor S1, and may be coupled with a separate drainage device that includes the remaining sensors S2 and S3. Such a separate drainage device may lack a drainage tube 305 and/or a flow controller 315.

In the embodiment shown, a pressure sensor S1 measures the pressure in the tube 305 upstream from the flow controller 315 and downstream from the posterior segment 178. In this manner, the pressure sensor S1 measures the pressure in the posterior segment 178. The expected measurement discrepancy between the true posterior segment pressure and that measured by S1 when located in a tube downstream of the posterior segment (even when located between the sclera and the conjunctiva) may be negligible.

A pressure sensor S2 is located at the drainage site 320 or in fluid communication with the drainage site 320 via the outlet tube 320. As such, the pressure sensor S2 may be located in the subconjunctival space, suprachoroidal space 200, a subscleral space, a supraciliary space, an episcleral vein, or another uveoscleral pathway, for example.

In some embodiments, the divider 310 acts as a barrier that separates the pressure region measured by the pressure sensor S3 from the pressure region measured by the pressure sensor S2. In some embodiments, the system includes other barriers that separate the sensors S1, S2, and S3. These barriers may be elements of the flow controller 315 itself. In FIG. 2, the pressure region measured by the pressure sensor S3 is physically separated from the pressure region measured by the pressure sensor S2 by the divider 310. The divider 310 is a physical structure that separates the drainage area 306 from the isolated location of pressure region measured by the pressure sensor S3. The divider 310 may be sutured and/or healed tissue.

Generally, IOP is a gauge pressure reading—the difference between the absolute pressure in the eye (as measured by sensor S1) and atmospheric pressure (as measured by sensor S3). Atmospheric pressure, typically about 760 mmHg, often varies in magnitude by 10 mmHg or more depending on weather conditions or indoor climate control systems or elevation changes. In addition, the effective atmospheric pressure can vary significantly—in excess of 300 mmHg—if a patient goes swimming, hiking, riding in an airplane, etc. Such a variation in atmospheric pressure is significant since IOP is typically in the range of about 15 mmHg. Thus, for accurate monitoring of IOP, it is desirable to have pressure readings for the interior chamber of the eye (as measured by sensor S1) and atmospheric pressure in the vicinity of the eye (as measured by sensor S3).

In one embodiment of the present invention, pressure readings are taken by the pressure sensors S1 and S3 simultaneously or nearly simultaneously over time so that the actual IOP can be calculated (as S1-S3 or S1-$f$(S3), where f(S3) indicates a function of S3). In another embodiment of the present invention, pressure readings taken by the pressure sensors S1, S2, and S3 can be used to control a device that drains aqueous from the posterior segment 178. For example, in some instances, the implant 300 reacts to the pressure differential across S1 and S3 continuously or nearly continuously so that the actual IOP (as S1-S3 or S1-$f$(S3)) can be responded to accordingly.

The drainage implant 300 may be shaped and configured to be implanted within the subconjunctival space, between the conjunctiva 202 and the sclera 180. In some embodiments, the bulk of the implant 300 may be positioned within the eye in a subconjunctival space between the conjunctiva 202 and the sclera 180 with the flow controller 315 positioned such that the implant does not come into contact with the optic nerve. For example, in one embodiment, depending upon the size and shape of the implant, the implant 300 may be positioned approximately 8 to 10 mm posterior to the limbus 190 (the border between the cornea and the sclera). The drainage implant 300 may be held in place within the eye via anchoring sutures, the angle of implantation and surrounding anatomy, or by a spring force or other mechanisms that stabilize the implant 300 relative to the patient's eye. In some embodiments, the inlet tube 325 and the outlet tube 330 are coupled to the flow controller 315 at the location of the subconjunctival space, and extend from the subconjunctival space into the posterior segment 178 and the delivery site, respectively.

Figure 3:
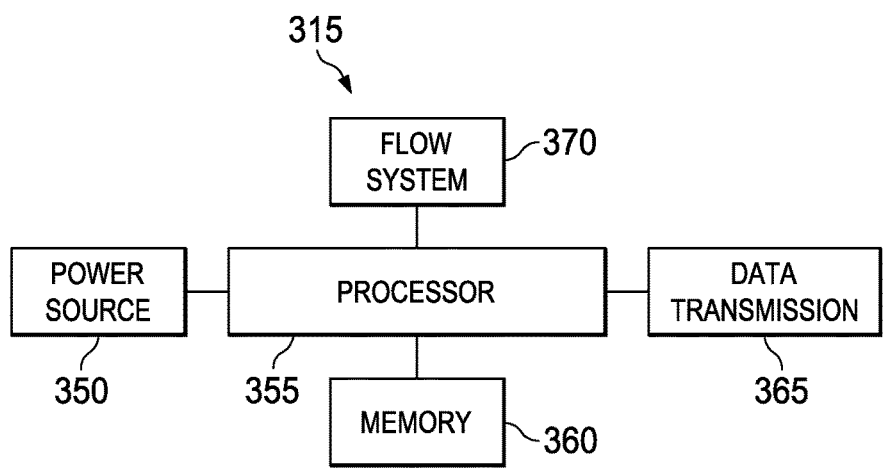
FIG. 3 is a block diagram illustrating elements of an exemplary flow controller according to one embodiment of the present disclosure.

FIG. 3 is a block diagram of an exemplary flow controller 315 forming a part of an implant implantable in an eye of a patient for the treatment of glaucoma or other conditions. The flow controller 315 is configured in a manner that provides IOP pressure control, but may also regulate and control bleb pressures, reducing complications arising from surgical implant glaucoma treatments. In FIG. 3, the flow controller 315 includes a power source 350, a processor 355, a memory 360, a data transmission module 365, and a flow system 370.

The power source 350 is typically a rechargeable battery, such as a lithium ion or lithium polymer battery, although other types of batteries may be employed. In addition, any other type of power cell is appropriate for power source 350. Power source 350 provides power to the flow controller 315, and more particularly to processor 355. Power source can be recharged via an RFID link or other type of magnetic coupling.

Processor 355 is typically an integrated circuit with power, input, and output pins capable of performing logic functions. In various embodiments, processor 355 is a targeted device controller. In such a case, processor 355 performs specific control functions targeted to a specific device or component, such as a data transmission module 365, power source 350, flow system 370, or memory 360. In other embodiments, processor 355 is a microprocessor. In such a case, processor 355 is programmable so that it can function to control more than one component of the device. In other cases, processor 355 is not a programmable microprocessor, but instead is a special purpose controller configured to control different components that perform different functions.

Memory 360 is typically a semiconductor memory such as NAND flash memory. As the size of semiconductor memory is very small, and the memory needs of the implant 300 are small, memory 360 occupies a very small footprint of the flow controller 315. Memory 360 interfaces with processor 355. As such, processor 355 can write to and read from memory 360. For example, processor 355 can be configured to receive data as signals from the sensors S1, S2, and S3 (FIG. 2) and write data to memory 360. In this manner, a series of measurements that may be indicative of IOP readings can be stored in memory 360. Processor 355 is also capable of performing other basic memory functions, such as erasing or overwriting memory 360, detecting when memory 360 is full, and other common functions associated with managing semiconductor memory.

Data transmission module 365 may employ any of a number of different types of data transmission. For example, data transmission module 365 may be an active device such as a radio. Data transmission module 365 may also be a passive device such as the antenna on an RFID tag. In this case, an RFID tag includes memory 360 and data transmission module 365 in the form of an antenna. An RFID reader can then be placed near the implant 300 to write data to or read data from memory 360. Since the amount of data typically stored in memory 360 is likely to be small (consisting of IOP readings over a period of time), the speed with which data is transferred is not crucial. Other types of data that can be stored in memory 360 and transmitted by data transmission module 365 include, but are not limited to, power source data (e.g. low battery, battery defect), speaker data (warning tones, voices), IOP sensor data (IOP readings, problem conditions), and the like.

Alternatively, data transmission module 365 may be activated to communicate an elevated IOP condition to a secondary device such as a PDA, cell phone, computer, wrist watch, custom device exclusively for this purpose, remote accessible data storage site (e.g. an internet server, email server, text message server), or other electronic device. In one embodiment, a personal electronic device uploads the data to the remote accessible data storage site (e.g. an internet server, email server, text message server). Information may be uploaded to a remote accessible data storage site so that it can be viewed in real time, for example, by medical personnel. For example, in a hospital setting, after a patient has undergone glaucoma surgery and had implant 300 implanted, a secondary device may be located next to the patient's hospital bed. Since IOP fluctuations are common after glaucoma surgery (both on the high side and on the low side which is also a dangerous condition), processor 355 can read IOP measurements made by the sensors S1, S2, and S3. If processor 355 determines that an unsafe IOP condition exists, data transmission module 365 can alert the patient and medical staff directly or by transmitting the unsafe readings to a secondary device.

The flow system 370 is the physical structure used to control the flow of fluid through the flow controller 315. It may include, for example, one or more pump mechanisms, valves, or other elements that help regulate the flow of fluid through the implant.

Figure 4A:
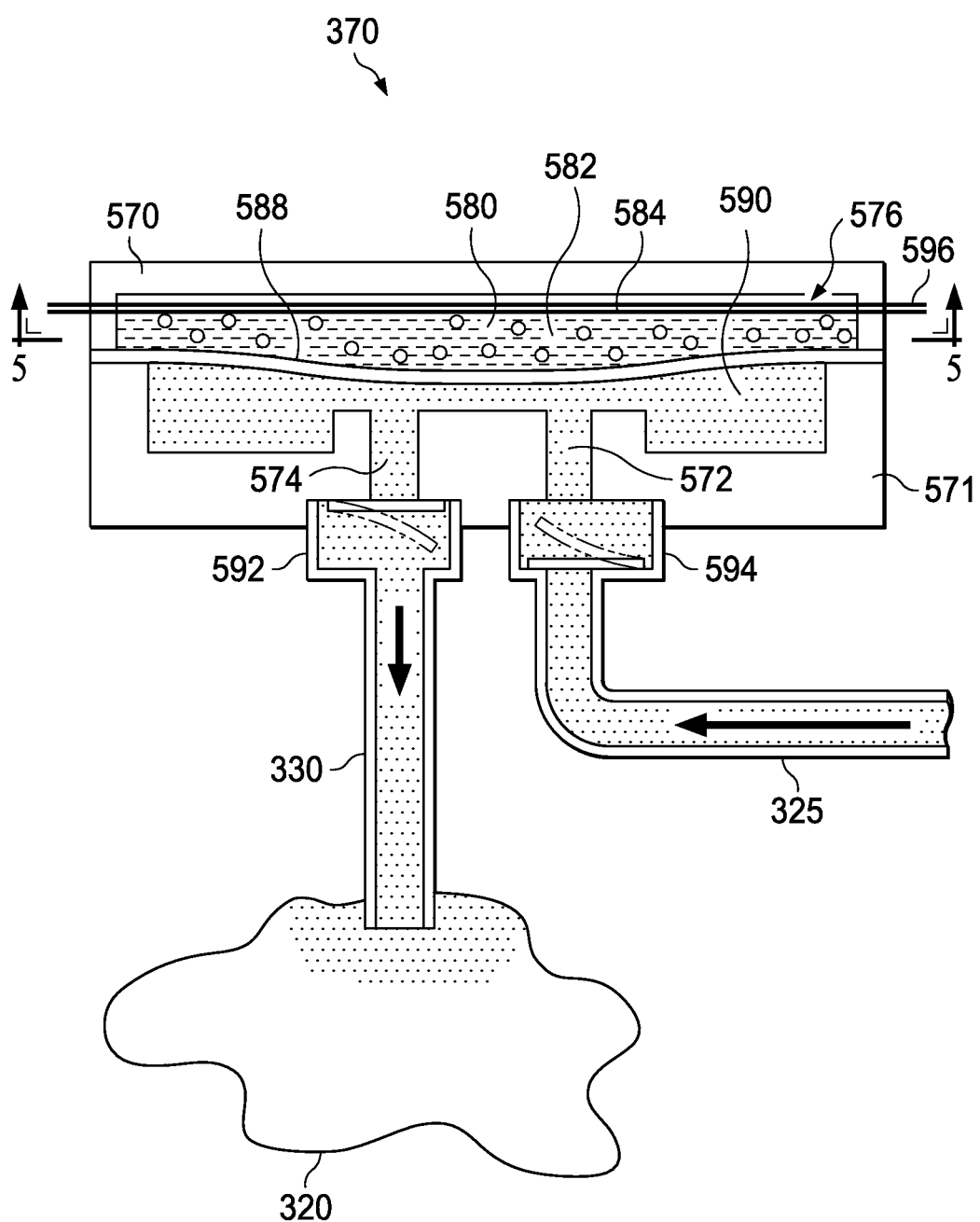
FIG. 4A illustrates a cross-sectional, schematic side view of an exemplary drainage implant with a flexible diaphragm in a position according to one embodiment of the present disclosure.
Figure 4B:
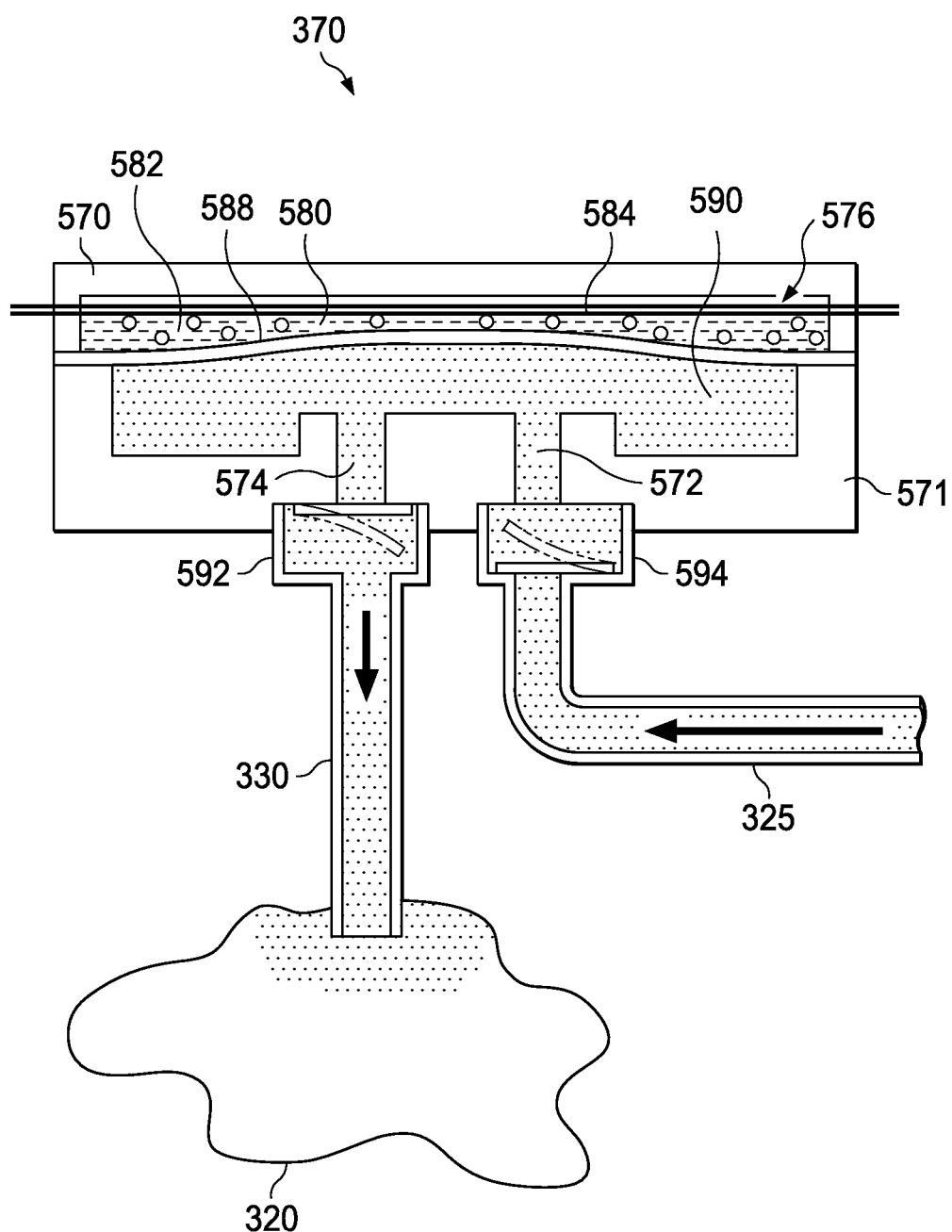
FIG. 4B illustrates a cross-sectional, schematic side view of an exemplary drainage implant with a flexible diaphragm in a position different than in FIG. 4A according to one embodiment of the present disclosure.

FIGS. 4A and 4B show an exemplary flow system 370 that may be used in the implant 300, connected to the inlet tube 325 and the outlet tube 330. The flow system 370 includes a flexible diaphragm 588 shown in FIG. 4A biased inward and shown in FIG. 4B biased outward. The flexible diaphragm 588 may be, for example, a Parylene or glass membrane, and may have a thickness ranging from 1 to 15 µm, although thicker and thinner diaphragms are contemplated. In the exemplary embodiment shown, the flow system 370 includes an upper housing 570 forming a part of a heating chamber 580, a lower housing 571 forming a part of a flow passage 590, an entrance port 572 in communication with the flow passage 590, and an exit port 574 in communication with the flow passage 590. The flexible diaphragm 588 is disposed between and separates the heating chamber 580 from the flow passage 590. Here, the entrance port 572 is in fluid communication with the inlet tube 325, and the exit port 574 is in fluid communication with the outlet tube 330. In some embodiments the outlet tube 330 is not present in the flow system 370, and the exit port 574 exits directly to the drainage site, which may include a bleb.

The upper and lower housings 570, 571, along with other aspects of the implant 300 and flow system 370 may be formed using MEMS (Micro-Electro-Mechanical Systems) technology.

In this embodiment, the flow system 370 is a pump 576 formed by the flexible diaphragm 188, a one-way check valve 592 adjacent the exit port 574, and a one-way check valve 594 adjacent the entrance port 572. Here, the check valves 592, 594 are formed of deformable cantilevers that prevent backflow. This ensures that drainage fluid travels one direction from the posterior segment of the eye toward the drainage site. It also ensures that fluid at the bleb does not reenter the flow system 370. Other embodiments include other types of check valves, such as ball valves, spring valves, reed valves, and others. Some embodiments include tapered openings at the flow passage entrance that decreases in cross-sectional area (according to flow direction) and the check valve 592 at the flow passage exit may include a narrow opening that increases in cross-sectional area. Accordingly, because of the shape of the openings, fluid flow will tend to flow easier out the exit port than out the entrance port—even in the absence of any movable parts such as flapper or reed valves.

Within the heating chamber 580, the flow system 315 includes an actuator fluid 582 that may be a liquid or gas, and a heating element 584. In some embodiments, the heating element 584 may be disposed adjacent the flexible diaphragm 588, and in some embodiments, may be in contact with the flexible diaphragm 588 to provide heat to the flow system 315. In the embodiment shown, the heating element is disposed adjacent the housing permitting the flexible diaphragm to flex without being inhibited by the possibly more rigid heating element. The heating element 584 can be powered by the power source under the control of the processor 355.

Figure 5:
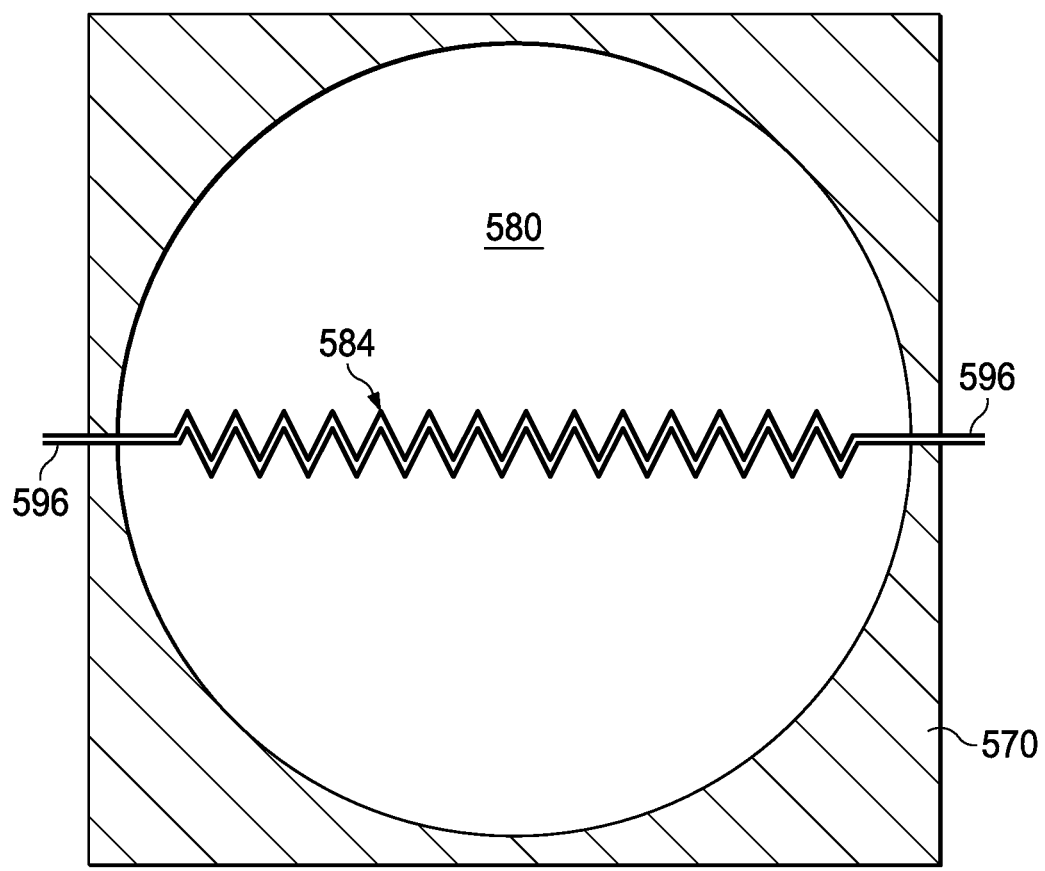
FIG. 5 illustrates a cross-sectional view of an exemplary drainage implant taken along lines 5-5 in FIG. 4A according to one embodiment of the present disclosure.

FIG. 5 shows a bottom view of the flexible diaphragm 588 and the heating element 584 on the upper housing 570, taken along lines 5-5 in FIG. 4A. With reference to FIGS. 4A, 4B, and 5, the flexible diaphragm 588 is disposed over the upper housing 570, which has a circular void that forms the heating chamber 580. The diaphragm 588 may deflect into or out of the heating chamber 580, as is apparent in FIGS. 4A and 4B.

The resistive heating element 584 extends across the heating chamber 580, and is in electrical connection with feed wires 596 that extend beyond the heating chamber 580 and diaphragm 588 to connect to the power source 350.

The fluid in the chamber may be a gas, such as air, or may be a fluid or gel. The fluid is selected to expand when subjected to heat to force the diaphragm to displace from a first position to a second position, such as from the position in FIG. 4B to the position shown in FIG. 4A. For example, as the temperature of the fluid in the heating chamber 580 expands, the volume of the flow passage 590 decreases. This forces fluid in the flow passage 590 to exit the flow passage 590 though the one-way check valve 592 toward the drainage site 320. As the temperature of the heating element 584 decreases, the temperature of the fluid in the heating chamber 580 decreases, and the volume correspondingly decreases. This causes the diaphragm 588 to move from its position in the flow passage 590, as is shown in FIG. 4A toward the heating chamber 580, increasing the volume of the flow passage as is shown in FIG. 4B. Accordingly, fluid may be drawn though the one way check valve 594 from the inlet tube 325.

The heating element may be a resistive heating element that converts electrical current to heat, and may be operated to gradually increase the volume of the pump chamber 429 as the fluid expands or to rapidly increase the volume of the pump chamber 429. When operated to slowly heat the fluid in the heating chamber, fluid flow from the flow passage can be gradual. When operated to rapidly increase the volume of the flow passage, fluid flow from the flow passage can be relatively rapid. This rapid movement of fluid can serve to clear blockages in the tubes or the drainage location. When the drainage site is a bleb, the rate at which fluid is expelled to the bleb can be controlled to maintain the bleb at a desirable size and/or pressure. In other words, by controlling fluid flow rates to the drainage site, the drainage site can be maintained in an optimal fashion.

In some embodiments, the heating element is simply turned off or not powered to permit the fluid to cool and gradually decrease in volume in order to reduce the volume of the heating chamber 580. When the heating element operates to gradually decrease the volume of the heating chamber 580, fluid flow from the inlet tube 325 into the flow passage 590 can be gradual. Both the speed of the deflection and the overall cycle frequency can be important in driving the flow.

In some embodiments, activation of the flow system 370 is based on the flow controller 315 comprising one or more electronic pressure sensors that may be located in pressure areas P1, P2, and/or P3 (shown in FIG. 2). If IOP is high, the flow controller 315 may determine that pumping action is desired in order to lower the IOP. To do this, electrical current is passed through the resistive heating element 584 to change the temperature of the fluid in the heating chamber 580. This in turn increases the volume of fluid in the heating chamber 580. To accommodate the increase in volume, the flexible diaphragm 588 expands into the flow passage 590, displacing the drainage fluid to force fluid out of the exit port 574. The current may then be stopped and the heating element may be allowed to cool to an ambient temperature, causing the flexible diaphragm to return to its original position. The cycle may then be repeated if additional pumping is determined to be desired. Accordingly, the pump 514 may be cycled or actuated a plurality of times to force the drainage fluid past the pump into the drainage site.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

I claim:

1. A system for treating an ocular condition comprising:
   a housing configured for ocular implantation;
   a heating chamber comprising a material expandable when heated;
   a flow passage having an inlet and an outlet;
   a heating element arranged and disposed to introduce heat in the heating chamber; and
   a flexible diaphragm separating the heating chamber from the flow passage, the flexible diaphragm being moveable between a first position and a second position to change a volume of one of the heating chamber and flow passages in response to a temperature change in the heating chamber.

2. The system of claim 1, wherein the heating element is a resistive heating element configured to increase in temperature when a current is passed therethrough.

3. The system of claim 1, wherein the heating element is disposed within the heating chamber.

4. The system of claim 1, wherein the heating element is a resistive heating element disposed along a wall of the heating chamber opposite the flexible diaphragm.

5. The system of claim 1, further comprising:
   a power source; and
   a feed wire extending on opposing sides of the heating element, the feed wire being in electrical communication with the power source.

6. The system of claim 1, further comprising at least one sensor arranged to detect a pressure indicative of intraocular pressure.

7. The system of claim 6, further comprising a processor configured to operate the heating element based on information detected by the at least one sensor.

8. The system of claim 1, further comprising a first one-way valve and a second one-way valve operable as the flexible diaphragm moves from the first position to the second position and back to the first position to promote the passage of drainage fluid through the flow passage in one direction.

9. The system of claim 8, wherein the first and second check valves are reed valves or flapper valves.

10. A system implantable in an eye for treating an ocular condition comprising:
    a housing configured for implantation in an eye of a patient, comprising:
    a sealed heating chamber;
    a fluid flow passage having an inlet and an outlet;
    a flexible diaphragm carried by the housing and disposed between and separating the heating chamber from the fluid flow passage;
    a heating element arranged and disposed to induce heat in the heating chamber to change pressure in the chamber; and
    a power source in electrical communication with the heating element and configured to induce electrical current in the heating element.

11. The system of claim 10, wherein the flexible diaphragm is moveable between a first position and a second position to change a volume of one of the heating chamber and flow passages in response to a temperature change in the heating chamber.

12. The system of claim 10, further comprising a fluid disposed in the heating chamber, the fluid being expandable when subjected to heat by the heating element.

13. The system of claim 10, wherein the heating element is a resistive heating element configured to increase in temperature when a current is passed therethrough.

14. The system of claim 10, wherein the heating element is disposed within the heating chamber.

15. The system of claim 10, wherein the heating element is a resistive heating element disposed along a wall of the heating chamber opposite the flexible diaphragm.

16. The system of claim 10, further comprising a first one-way valve and a second one-way valve operable as the flexible diaphragm moves from the first position to the second position and back to the first position to promote the passage of drainage fluid through the flow passage in one direction.

17. A method for treating an ocular condition comprising:
implanting a flow control device in an ocular cavity;
inducing flow of a liquid through a flow pump having a flexible diaphragm separating a flow passage from a heating chamber;
moving the flexible diaphragm from a first position to a second position by increasing a temperature of a fluid in the heating chamber;
forcing fluid from the flow passage as the flexible diaphragm moves the first position to the second position; and
drawing fluid into the flow passage by moving the flexible diaphragm from the second position to the first position.

18. The method of claim 17, wherein moving the flexible diaphragm by increasing a temperature of a fluid in the heating chamber comprises applying voltage to a heating element disposed in a closed chamber.

19. The method of claim 17, further comprising drawing fluid into the flow passage through a first one-way valve and pushing fluid out of the flow passage through a second one-way valve.

20. The method of claim 17, further comprising implanting the flow pump in an eye of a patient.

* * * * *